United States Patent
Inoue et al.

(10) Patent No.: US 10,226,170 B2
(45) Date of Patent: Mar. 12, 2019

(54) VISION TESTING DEVICE

(71) Applicant: CREWT MEDICAL SYSTEMS, INC., Tokyo (JP)

(72) Inventors: Satoshi Inoue, Tokyo (JP); Kenzo Yamanaka, Tokyo (JP); Shinji Kimura, Tokyo (JP)

(73) Assignee: CREWT MEDICAL SYSTEMS, INC., Tokyo (JP)

( * ) Notice: Subject to any disclaimer, the term of this patent is extended or adjusted under 35 U.S.C. 154(b) by 0 days.

(21) Appl. No.: 15/520,777

(22) PCT Filed: Aug. 18, 2015

(86) PCT No.: PCT/JP2015/073080
§ 371 (c)(1),
(2) Date: Apr. 20, 2017

(87) PCT Pub. No.: WO2016/063602
PCT Pub. Date: Apr. 28, 2016

(65) Prior Publication Data
US 2017/0332896 A1    Nov. 23, 2017

(30) Foreign Application Priority Data
Oct. 20, 2014    (JP) .................................. 2014-214017

(51) Int. Cl.
*A61B 3/14*  (2006.01)
*A61B 3/024*  (2006.01)
(Continued)

(52) U.S. Cl.
CPC .............. *A61B 3/024* (2013.01); *A61B 3/005* (2013.01); *A61B 3/032* (2013.01); *A61B 3/14* (2013.01);
(Continued)

(58) Field of Classification Search
CPC .. A61B 3/02; A61B 3/08; A61B 3/005; A61B 3/0008; A61B 3/024; A61B 3/025;
(Continued)

(56) References Cited

U.S. PATENT DOCUMENTS 5,035,474 A * 7/1991 Moss .................... G02B 27/01
359/13
2010/0026714 A1    2/2010 Utagawa

FOREIGN PATENT DOCUMENTS

JP        0767833 A * 3/1995 ............. A61B 3/024
JP      H07-67833 A    3/1995
(Continued)

OTHER PUBLICATIONS

Nov. 17, 2015 International Search Report issued in International Patent Application No. PCT/JP2015/073080.
(Continued)

*Primary Examiner* — Mustak Choudhury
(74) *Attorney, Agent, or Firm* — Oliff PLC (57) ABSTRACT

A small-sized head-mount type vision testing device, which is mounted on a testee's head, including: a display device that presents a visual target to an eyeball of the testee; a display optical system that guides light of the visual target presented on the device to the retina; an imaging device that images the eyeball; and an observation optical system that guides an image of the eyeball to the imaging device, and further including a mirror that reflects light of a specific wavelength and transmits the other light at a point closer to the eyeball side than the display device, wherein an optical axis from a pupil to the mirror in the display optical system and an optical axis from the pupil to the mirror in the observation optical system, coincide with each other, and the optical axes are bent through the mirror.

5 Claims, 5 Drawing Sheets

(51) Int. Cl.
  *A61B 3/00* (2006.01)
  *A61B 3/032* (2006.01)
  *A61B 3/10* (2006.01)
  *A61B 3/06* (2006.01)
  *A61B 3/11* (2006.01)

(52) U.S. Cl.
  CPC .................. *A61B 3/063* (2013.01); *A61B 3/10* (2013.01); *A61B 3/112* (2013.01)

(58) Field of Classification Search
  CPC ..... A61B 3/032; A61B 3/0041; A61B 3/0058; A61B 3/0075; A61B 3/0033; A61B 3/0091; A61B 3/112; A61B 3/113; A61B 3/145; A61B 3/165; A61B 3/12; A61B 3/14; A61B 3/16; A61B 3/028; A61B 3/1015; A61B 3/1035; A61B 5/04842; A61B 5/14555; G02B 27/0093; G02B 27/0172
  USPC .......................... 351/201–212, 224, 239, 246
  See application file for complete search history.

(56) References Cited

FOREIGN PATENT DOCUMENTS

| JP | H09-218375 A | 8/1997 |
| JP | H10-179520 A | 7/1998 |
| JP | H10-319240 A | 12/1998 |
| JP | H10-319343 A | 12/1998 |
| JP | H11-225964 A | 8/1999 |
| JP | 2007-286269 A | 11/2007 |
| JP | 2010-039556 A | 2/2010 |
| JP | 2011-085829 A | 4/2011 |

OTHER PUBLICATIONS

Jun. 27, 2018 Search Report issued in European Patent Application No. 15852209.4.

* cited by examiner

VISION TESTING DEVICE

TECHNICAL FIELD

The present invention relates to a vision testing device.

DESCRIPTION OF RELATED ART

Humphrey perimeter is known as a vision testing device that performs visual field test to diagnose symptoms of field narrowing such as glaucoma. The Humphrey perimeter has a dome type screen. In the visual field test, a testee fixes a head to a pedestal provided in front of the screen. Then, when the visual target is presented on the screen, the testee himself/herself answers whether the visual target has been visible or not, thereby measuring the visual field of the testee.

In order to measure an entire visual field of the testee, it is necessary to present the visual target over a wide angle (viewing angle) to an eyeball. In the Humphrey perimeter, since no optical system such as a lens is provided between the eyeball of the testee and the dome type screen, a wide screen is required to present the visual target over a wide angle to the eyeball. As a result, a size of an entire body of the Humphrey perimeter is increased, and there is a need for a wide installation place for installing the Humphrey perimeter and a dark room for accommodating the Humphrey perimeter and the testee in a dark space.

Therefore, in order to solve a problem of increasing the size of the Humphrey perimeter, a head-mount type vision testing device to be mounted on the testee's head is proposed (for example, Patent Document 1). The vision testing device of patent document 1 includes a measurement unit having a display device for presenting a visual target to an eyeball of a testee; a lens for guiding the light of the visual target presented on the display device to the eyeball; a half mirror; and an imaging device for imaging an eyeball in order to align a position of the display device. The measurement unit is installed in a goggle type frame mounted on the testee's head.

PRIOR ART DOCUMENT

Patent Document

Japanese Patent Laid Open Publication No. 1995-67833

SUMMARY OF THE INVENTION

Problem to be Solved by the Invention

However, in the configuration of patent document 1, there is a possibility that the size of a head-mount type vision testing device is increased, because a large-sized display device is required, for the following reason.

According to a background art of patent document 1, it is a mainstream to arrange the display device so as to face the eyeballs of the testee, in an ordinary head mount display aiming only to display images. Therefore, in the head-mount type vision testing device of patent document 1 as well, the display device is arranged so as to face the eyeballs of the testee while the optical axis on the imaging device side is arranged so as to be bent through the half mirror. Further, an image on the display device is formed on the retina of the testee using only one lens. In the head-mount type vision testing device of patent document 1 having such a configuration, in order to present the visual target over a wide angle to the eyeball, a large-sized display device is required. As a result, there is a possibility that the size of the measurement unit for accommodating the display device is increased, and an entire size of the vision testing device is increased.

Therefore, a main object of the present invention is to provide a small-sized head-mount type vision testing device.

Problem to be Solved by the Invention

According to a first aspect of the present invention, there is provided a vision testing device, which is a head-mount type vision testing device mounted on a testee's head, including:

a display device that presents a visual target to an eyeball of the testee;

a display optical system that guides a light of the visual target presented on the display device, to a retina of the eyeball;

an imaging device that images the eyeball; and an observation optical system that guides an image of the eyeball to the imaging device, the display optical system further comprising a mirror that reflects a light of a specific wavelength and transmits the other light at a point closer to the eyeball side than the display device, wherein an optical axis from a pupil of the eyeball to the mirror in the display optical system and an optical axis from the pupil to the mirror in the observation optical system, coincide with each other, and the optical axis from the pupil of the eyeball to the mirror in the display optical system and an optical axis from the mirror to the display device in the display optical system, are bent through the mirror.

According to a second aspect of the present invention, there is provided the vision testing device of the first aspect, wherein the optical axis from the mirror to the display device in the display optical system, is inclined toward a head side than a direction vertical to the optical axis from a pupil of the eyeball to the mirror in the display optical system.

According to a third aspect of the present invention, there is provided the vision testing device of the first or second aspect, wherein when an angle formed by the optical axis from the pupil of the eyeball to the mirror in the display optical system, and the optical axis from the mirror to the display device in the display optical system, is represented by a, the following formula (1) is satisfied:

$$40° < \alpha < 90° \quad (1).$$

According to a fourth aspect of the present invention, there is provided the vision testing device of any one of the first to third aspects, wherein the display optical system includes:

a first lens provided between the eyeball and the mirror and having an optical axis passing through a center of the pupil of the eyeball; and a second lens group provided between the mirror and the display device and provided on an optical axis in a direction reflecting through the mirror with respect to the optical axis at the first lens, wherein the observation optical system shares the first lens with the display optical system.

According to a fifth aspect of the present invention, there is provided the vision testing device of the fourth aspect, wherein a focal length of the first lens is shorter than an optical distance from the first lens to the second lens group.

According to a sixth aspect of the present invention, there is provided the vision testing device of fourth or fifth aspect, wherein a power of the first lens is 20D or more and 60D or less.

According to a seventh aspect of the present invention, there is provided the vision testing device of any one of the first to sixth aspects, wherein a diagonal length of the display device is 1.5 inches or less.

Advantage of the Invention

According to the present invention, a small-sized head-mount type vision testing device can be provided.

DETAILED DESCRIPTION OF THE INVENTION

Embodiments of the present invention will be described hereafter, with reference to the drawings.

Figure 1:
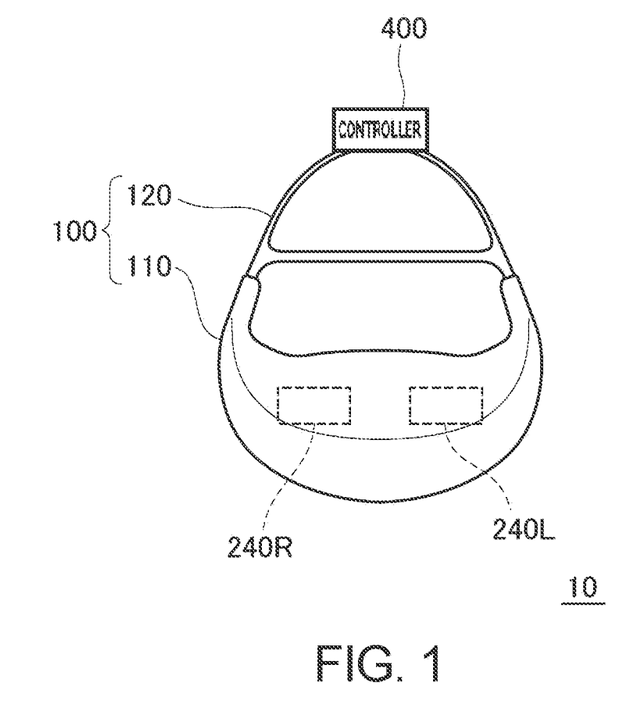
FIG. 1 is a schematic view of a vision testing device according to an embodiment.

In this embodiment, an explanation is given in the following order.
1. Vision testing device
   1-1. Display optical system and display device
   1-2. Optical characteristic, etc., of the display optical system
   1-3. Observation optical system and imaging device
   1-4. Controller
2. Vision testing method
3. Effect of the embodiment
4. Modified example, etc.
1. Vision Testing Device FIG. 1 is a schematic view of a vision testing device according to an embodiment. As shown in FIG. 1, a vision testing device 10 of this embodiment is configured as a head-mount type vision testing device to be mounted on a head of a testee who undergoes a visual field test. Specifically, the vision testing device 10 includes, for example a head mount (HM) unit 100 and a controller 400.

The HM unit 100 includes a casing (mounting body) 110 and a mounting fixture 120 connected to the casing 110, and is configured to be mountable to the testee's head by the mounting fixture 120. In the casing 110, a display optical system (200) and an observation optical system (300), etc., which will be described later are stored. For example, the display optical system (200) is provided for each of the eyes. In the casing 110, a display device 240 R corresponding to the right eye and a display device 240 L corresponding to the left eye are provided. Further, the mounting fixture 120 includes a first belt wound in a U-shape from both sides of a head to a rear head side of the testee, and a second belt wound around a head top of the testee. The second belt may be configured to be adjustable in length.

The controller 400 is configured to control the display optical system (200) and the observation optical system (300), etc. Further, the controller 400 is arranged, for example on the rear head side of the mounting fixture 120. Thereby, it is possible to maintain a weight balance in the front and rear of the casing 110 and the controller 400.

Figure 2:
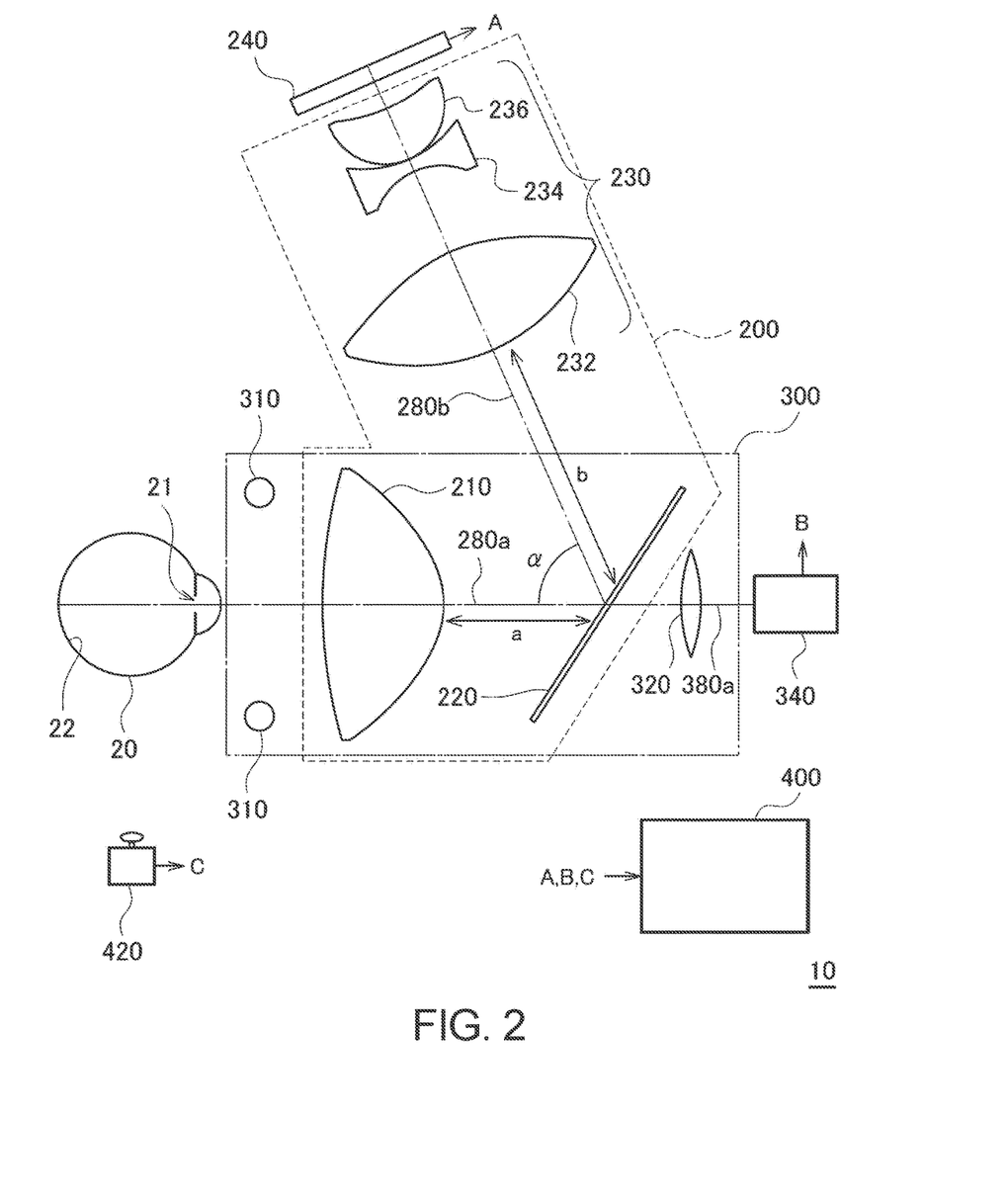
FIG. 2 is a schematic cross-sectional view of the vision testing device according to an embodiment.

FIG. 2 is a schematic cross-sectional view of the vision testing device according to this embodiment. As shown in FIG. 2, the vision testing device 10 of this embodiment has the display optical system 200 for presenting a visual target to an eyeball 20 and an observation optical system 300 for imaging the eyeball 20. In this embodiment, in order to decrease a size of the vision testing device 10, the display optical system 200 is bent. Detailed explanation is given in detail hereafter.

In FIG. 2, the optical system (the display optical system 200 and the observation optical system 300) corresponding to one eye is shown, and for example the optical system corresponding to each of the left and right eyes has the same configuration. In the description hereafter, the optical system corresponding to each of the left and right eyes is described without distinction, and letters L and R are omitted.

Further, explanation is given hereafter on the assumption that the light is emitted from a position of a retina 22 through a pupil 21 (assuming the pupil 21 to be an exit pupil) in some cases. A case where an image of the light emitted from the retina 22 is formed on the display device 240 and a case where an image of the light emitted from the display device 240 is formed on the retina 22 have the same meaning in the optical system of this embodiment. Hereinafter, the case where light is actually emitted from the position of the display device 240 is referred to as "a case of a forward ray from the display device 240", and a case where light is emitted from the position of the retina 22 will be described as "a case of a backward ray from the retina 22".

(1-1. Display Optical System and Display Device)

The display optical system 200 is configured to guide a light of a predetermined visual target to the retina 22 of the eyeball 20. The term "visual target" as used herein refers to a point or figure presented to the eyeball of the testee at the time of a visual field test. The display optical system 200 has, for example a first lens 210, a mirror 220, and a second lens group 230 in an order from the eyeball 20 side.

The first lens 210 functions as an objective lens when the eyeball 20 is an object, and is configured as a positive lens for example. An optical axis 280a of the first lens 210 is arranged to pass through a center of the pupil 21 of the eyeball 20 (the center of the eyeball 20).

The first lens 210 has a large positive refractive power (power) so as to converge the light from the retina 22 in a predetermined range in the case of a backward ray from the retina 22. In the case of the backward ray from the retina 22, a light flux of a principal ray from the retina 22 passing through an edge of the first lens 210 is bent by the first lens 210, the image of the light flux of the principal ray from the retina 22 is formed (collected) at the position near the mirror 220. All lights from the retina 22 over a wide angle is converged by the first lens 210 within a range of the mirror 220. Details of the power of the first lens 210 will be described later.

The mirror 220 is configured to reflect a light of a specific wavelength and transmit the other light. Specifically, the mirror 220 is configured as, for example a cold mirror that reflects a visible light and transmits an infrared light. The mirror 220 is provided on the side opposite to the eyeball 20 with the first lens 210 interposed therebetween (interposing the first lens 210) on the optical axis 280a of the first lens 210. Further, the mirror 220 is provided so as to be inclined at a predetermined angle with respect to the optical axis 280a of the first lens 210, and in the case of the backward ray coming from the retina 22, the mirror 220 is configured to reflect the light converged at the position near the mirror 220 in a predetermined direction. On the other hand, the mirror 220 is configured to transmit the infrared light reflected on the surface of the eyeball 20 described later to the opposite side of the eyeball 20 with the mirror 220 interposed therebetween.

In the case of the backward ray from the retina 22, the second lens group 230 is configured to function as a relay system that forms the image of the light again on the display device 240, the image of light from the retina 22 being previously formed at the position near the mirror 220 by the first lens 210, and further configured to correct chromatic aberration and magnification.

The second lens group 230 is provided on the optical axis 280b in a direction of reflecting through the mirror 220 with respect to the optical axis 280a of the first lens 210. In other words, the optical axis 280a from the pupil 21 of the eyeball 20 to the mirror 220 in the display optical system 200, and the optical axis 280b from the mirror 220 to the display device 240 in the display optical system 200, are bent in a direction of mutually reflecting through the mirror 220. In this embodiment, for example, the optical axis 280b from the mirror 220 to the display device 240 in the display optical system 200 is positioned vertically above the optical axis 280a from the pupil 21 of the eyeball 20 to the mirror 220 in the display optical system 200, on a vertical plane including the optical axis 280a from the pupil 21 of the eyeball 20 to the mirror 220 in the display optical system 200. The optical axis 280b from the mirror 220 to the display device 240 in the display optical system 200 is inclined toward a head side from a direction vertical to the optical axis 280a from the pupil 21 of the eyeball 20 to the mirror 220 in the display optical system 200. As a result, a center of gravity of the second lens group 230 and the display device 240 is close to the head side, and it is possible to improve the weight balance of the vision testing device 10 as a whole.

Here, when an angle formed by the optical axis 280a from the pupil 21 of the eyeball 20 to the mirror 220 in the display optical system 200 and the optical axis 280b from the mirror 220 to the display device 240 in the display optical system 200 is set to α, the following formula (1) is satisfied.

$$40° < \alpha < 90° \tag{1}$$

In the case of α≤40°, there is a possibility that the second lens group 230 and the display device 240 are too close to the head and interfere with the head. In contrast, by satisfying α>40°, it is possible to prevent the second lens group 230 and the display device 240 from interfering with the head. On the other hand, in the case of α≥90°, there is a possibility that the vision testing device 10 is easily falling-off from testee's head when the testee tilts the head forward. In contrast, by satisfying α<90°, even when the testee tilts the head forward, it is possible to suppress the vision testing device 10 from falling-off from the head of the testee.

Further, it is preferable to satisfy the following formula (2).

$$50° \leq \alpha \leq 80° \tag{2}$$

By satisfying α≥50°, it is possible to prevent the second lens group 230 and the display device 240 from interfering with a forehead even if the testee has a protruding forehead. On the other hand, by satisfying α≤80°, the center of gravity of the second lens group 230 and the display device 240 is reliably positioned on the head side, and it is possible to improve the weight balance of the vision testing device 10 as a whole.

Further, it is preferable to satisfy the following formula (3).

$$60° \leq \alpha \leq 70° \tag{3}$$

By setting α≥60°, even in a case of the testee whose forehead portion is protruding and eye curving is deep, the second lens group 230 and the display device 240 can be prevented from interfering with the forehead portion. On the other hand, by satisfying α≤70°, the center of gravity of the second lens group 230 and the display device 240 is positioned closer to the head side than the above, and it is possible to further improve the weight balance of the vision testing device 10 as a whole. Further, since a normal direction of the mirror 220 approaches the optical axis 280a of the first lens 210, a range of the light irradiated from the first lens 210 to the mirror 220 can be decreased, and it is possible to reduce a required diameter of the mirror 220 in the vertical direction. Therefore, the size of the vision testing device 10 can be decreased.

In addition, the second lens group 230 includes at least a lens having a positive refractive power and a lens having a negative refractive power. Thereby, it is possible to correct the chromatic aberration of the display optical system 200. Specifically, for example, the second lens group 230 includes a positive lens 232, a negative lens 234, and a positive meniscus lens 236 that is convex toward the eyeball 20 side, in an order from the side of the eyeball 20. An outer diameter of the positive lens 232 is larger than outer diameters of the negative lens 234 and the positive meniscus lens 236, and an outer diameter of the negative lens 234 is substantially equal to an outer diameter of the positive meniscus lens 236. With such a lens configuration, the chromatic aberration of the display optical system 200 can be corrected.

The display device 240 is configured to present a predetermined visual target to the eyeball 20. The predetermined visual target is, for example a fixed target such as a cross shape, a stimulus target having a predetermined brightness (luminance) for a visual field test, or the like. The display device 240 is configured as a liquid crystal display device, an organic LED display device, or the like, for example. In addition, the display device 240 is configured to be capable of presenting a high luminance visual target for the visual field test, and a maximum luminance of the display device 240 is, for example 3000 cd/m² or more.

The display device 240 is provided on the side opposite to the mirror 220 with the second lens group 230 interposed therebetween on the optical axis 280b of the second lens group 230. A display surface of the display device 240 is arranged such that its normal direction coincides with the optical axis 280b of the second lens group 230. The display device 240 is arranged such that in a case of the backward ray from the retina 22, the image of the light from the retina 22 is formed on the display device 240 via the first lens 210, the mirror 220 and the second lens group 230. In other words, the display device 240 is arranged at a position optically conjugate with the retina 22 via the first lens 210, the mirror 220 and the second lens group 230.

Further, the display device 240 is connected to the controller 400 and is configured to present a predetermined visual target to the eyeball 20, based on a signal from the controller 400.

(1-2. Optical Characteristics, Etc., of the Display Optical System)

Here, the optical characteristics, etc., of the display optical system 200 will be described in detail.

(First Lens)

The first lens 210 has a large positive refractive power (power) as described above and satisfies the following condition.

When the distance from the first lens 210 to the mirror 220 is set to a, the distance from the mirror 220 to the second lens group 230 is set to b, and the optical distance from the first lens 210 to the second lens group 230 is set to D1, $D1=a+b$ is established.

When the focal length of the first lens 210 is set to f1, the focal length f1 of the first lens 210 is shorter than the optical distance D1 from the first lens 210 to the second lens group 230, namely, the following formula (4) is satisfied.

$$f1<D1 \tag{4}$$

Further, when the focal length of the second lens group 230 is f2, the focal length f1 of the first lens 210 and the focal length f2 of the second lens group 230 satisfy the following formula (5).

$$0<f1/f2<1.0 \tag{5}$$

Further specifically, the power of the first lens 210 is 20D (diopter) or more and 60D or less. Due to the power of the first lens 210, the distance between the position of the pupil 21 and the first lens 210 is changed. When the power of the first lens 210 is less than 20D, the pupil and the first lens are separated from each other, and a deflection angle of a ray becomes further small. Therefore, in order to cause all lights from the retina to be reflected by the mirror in the case of the backward ray from the retina, there is a possibility that the size of the mirror becomes large. In the vision testing device, it is necessary to install the mirror in front of each of the eyes. Therefore, in the case that the inter-pupil distance (about 50 mm) of the testee is taken into consideration, there is a possibility that members such as a lens barrel that holds a mirror in each of both eyes will interfere with each other when the size of the mirror becomes excessively large. In contrast, since the power of the first lens 210 is 20D or more in the case of the backward ray from the retina, the light from the retina 22 over a wide angle can be converged by the first lens 210 within a range of the mirror 220, and it is possible to form an image of the light from the retina 22 through the mirror 220 and the second lens group 230 on the display device 240 having a predetermined size. Accordingly, the size of the mirror can be decreased, and it is possible to prevent the members such as the lens barrel that holds a mirrors for each of both eyes from interfering with each other even in consideration of the inter-pupil distance (about 50 mm) of the testee. On the other hand, when the power of the first lens 210 is greater than 60D, the distance between the pupil and the first lens becomes too close, and there is a possibility that the first lens will interfere with the testee's eyelashes and eyelids. In this case, there is a possibility that the testee may be uncomfortable and accurate visual field test may not be possible. Further, the first lens is easily contaminated or scratched, and therefore there is a possibility that accuracy of the visual field test may be deteriorated. In contrast, when the power of the first lens 210 is 60D or less, it is possible to prevent the first lens 210 from interfering with the eyelashes and eyelids of the testee. Further, contamination and scratches on the first lens can be suppressed, and deterioration of the accuracy of visual field test can be suppressed.

Further, in order to present the visual target over a wide angle to the eyeball 20, a further larger first lens 210 is preferable. However, the distance between both eyes of a human being is about 50 mm, and therefore the diameter of the first lens 210 is, for example 50 mm or less so that the first lenses 210 of both eyes do not interfere with each other.

Further, a maximum viewing angle of the display optical system 200 using the first lens 210 (the maximum value of the angle formed by the principal ray passing through the center of the pupil 22 and the optical axis 280a) is preferably 30 degrees or more and 60 Degrees or less in half angle of view (60 Degrees or more and 120 degrees or less in full angle of view).

(Display Device)

By increasing the power of the first lens 210 as described above, the size of the display device 240 on which the image of the light from the retina 22 is formed in the case of the backward ray from the retina 22, can be decreased to a predetermined size. Specifically, a diagonal length (on the display surface) of the display device 240 is, for example 1.5 inches or less, and preferably 1.0 inches or less. By making the display device 240 small, the vision testing device 10 can be made small.

(Chromatic Aberration Characteristics)

In order to suppress the chromatic aberration of the display optical system 200, the first lens 210 and the second lens group 230 have the following optical characteristics.

When the Abbe number of the first lens 210 is set to v1, the following formula (6) is satisfied. The larger the Abbe number is, the smaller the dispersion of the lens is.

$$45<v1<80 \tag{6}$$

When the Abbe number of the lens having a positive refractive power (for example, the positive lens 232, the positive meniscus lens 236) in the second lens group 230 is set to v2, the following formula (7) is satisfied.

$$45<v2<80 \tag{7}$$

Further, when the Abbe number of the lens having a negative refractive power (for example, the negative lens 234) in the second lens group 230 is set to v3, the following formula (8) is satisfied.

$$15<v3<30 \tag{8}$$

By satisfying the formulas (6) to (8), the chromatic aberration of the display optical system 200 can be suppressed.

Further, each lens of the first lens 210 and the second lens group 230 has an aspheric surface. Thereby, various aberrations can be suppressed, and the size of the display optical system 200 can be decreased. However, it is not necessary to make all the lenses constituting the display optical system 200 as aspherical lenses, and the display optical system 200 can be realized by a combination of a plurality of spherical lenses or a combination of the spherical lens and the aspheric lens, for example. In this case, among the plurality of lenses constituting the display optical system 200, it is preferable to constitute at least a lens closest to an eyeball position (the first lens 210 in the example of this embodiment) by the aspherical lens. The reason is that when the lens closest to the eyeball position is constituted by the aspheric lens, the degree of freedom of optical design is increased as compared with a case where the lens is constituted by a spherical lens, reduction of the number of lenses is expected, and the size of the vision testing device 1 can be decreased and a weight thereof can be decreased. Particularly, the fact that the optical path from the position of the eyeball to the mirror 220 becomes long, corresponds to the fact that the casing 110 becomes longer in front of the testee, thereby causing a problem that it becomes difficult to secure the weight balance. For this reason, it is preferable that the lens closest to the eyeball position is the aspheric lens and a protrusion amount in a forward direction is as small as possible.

(1-3. Observation Optical System and Imaging Device)

The observation optical system 300 is configured to guide the image of the eyeball 20 (images of the iris and the pupil 21, etc.) to the imaging device 340. Specifically, the observation optical system 300 includes, for example, a light source 310, a first lens 210 shared with the display optical system 200, a mirror 220 shared with the display optical system 200, and an imaging lens 320, in an order from the eyeball 20 side.

A light source 310 for illuminating the eyeball 20 is provided between the eyeball 20 and the first lens 210 at a position outside of a ray passage range of the first lens 210. For example, two light sources 310 are provided in a horizontal direction (or a vertical direction) with the eyeball 20 interposed therebetween. The light source 310 is configured as an LED light source that performs irradiation of an infrared light, for example. By irradiating the eyeball 20 with infrared light, the eyeball 20 of the testee can be imaged without being sensed by the retina 22 of the testee.

In the observation optical system 300, the first lens 210 and the mirror 220 are shared with the display optical system 200, and therefore the optical axis 280a from the pupil 21 of the eyeball 20 to the mirror 220 in the display optical system 200, coincides with the optical axis (280a) from the pupil 21 of the eyeball 20 to the mirror in the observation optical system 300. Further, as described above, the mirror 220 is configured to transmit the infrared light irradiated from the light source 310 and reflected on the surface of the eyeball 20.

The imaging lens 320 is configured as a relay lens that forms the image of the infrared light transmitted through the mirror 220, on the imaging device 340. The optical axis 380a of the imaging lens 320 coincides (the optical axis 380a of the imaging lens 320 is located on the same axis as the optical axis 380a of the first lens 210) with the optical axis 380a of the first lens 210. Further, the imaging lens 320 is configured so that the image of the pupil 21 of the eyeball 20 is focused on the imaging device 340.

The imaging device 340 is configured to image the eyeball 20 by detecting the infrared light, specifically, for example, configured as a CCD (Charge Coupled Device) or CMOS (Complementary Metal Oxide Semiconductor). The imaging device 340 is provided on the opposite side of the mirror 220 with the imaging lens 320 interposed therebetween on the optical axis 380a of the imaging lens 320. The imaging surface of the imaging device 340 is arranged so that its normal direction coincides with the optical axis 380a of the imaging lens 320. Further, the imaging device 340 is connected to the controller 400, and is configured to transmit the image of the eyeball 20, to the controller 400.

(1-4. Controller)

The controller (computer unit) 400 is provided for performing an operation control necessary for the visual field test, and is composed of a combination of CPU (Central Processing Unit), RAM (Random Access Memory), ROM (Read Only Memory), HDD (Hard Disk Drive), and various interfaces. Then, the controller 400 is configured to function as various units by executing a predetermined program stored in the ROM ore the HDD by the CPU.

The controller 400 is connected to the display device 240 and the imaging device 340 so as to be able to communicate with each other by either wired or wirelessly (A, B), and is configured to control the display device 240 and the imaging device 340.

Here, the vision testing device 10 of this embodiment is configured to be able to perform a subjective visual field test described later, and the controller 400 is configured to function as a sensitivity mapping unit.

For example, in the vicinity of the testee, a switch 420 is provided for the testee to reply whether the visual target becomes visible or not. The switch 420 is connected to the controller 400 (C) and is configured to transmit a signal to the controller 400, to indicate that the testee has visually recognized the visual target.

The sensitivity mapping unit of the controller 400 has a function of mapping a luminance of the display device 240 as the sensitivity of the retina 22 when the visual target becomes visible, based on the signal transmitted from the switch 420.

Further, the vision testing device 10 of this embodiment is also configured so as to be able to perform an objective visual field test described later, and the controller 400 is configured to function as a visual target presentation unit, a miosis pupil detection unit, and a sensitivity mapping unit.

The target presentation unit has a function of causing the display device 240 to present the visual target.

The miosis pupil detection unit has a function of detecting a miosis of the pupil 21 when a brightness of the visual target presented by the display device 240 becomes equal to or higher than the predetermined brightness (luminance), based on the image of the pupil 21 acquired by the imaging device 340.

The sensitivity mapping unit has a function used not only in the subjective visual field test but also in the objective visual field test, and has a function of mapping the brightness (luminance) of the visual target presented by the display device 240 as the sensitivity of the retina 22 when the miosis detection unit detects the miosis of the pupil 21.

A predetermined program for realizing each of these functions is installed in the controller 400 and used, but prior to the installation, it may be stored in a storage medium readable by the controller 400, or may be provided to the controller 400 through a communication line connected to the controller 400.

In addition, the controller 400 in which the predetermined program is installed may not necessarily be installed in the vision testing device 10 as long as it can give an operation control command to each unit of the vision testing device 10, or may be connected to the vision testing device 10 via a communication line.

<2. Vision Testing Method>

Dynamic quantitative visual field test, static quantitative visual field test, fundus visual field test (microperimetry), electroretinography (ERG) and other test can be performed by the vision testing device 10 of this embodiment. A case of performing the static quantitative visual field test will be described hereafter. Regarding the static quantitative visual field test, there are a subjective visual field test and the objective visual field test, and the vision testing device 10 of this embodiment can perform any type of these tests.

The subjective visual field test is performed as follows. First, an HM unit 100 of the vision testing device 10 is mounted on the testee's head, so that the testee holds the switch 420. The target presentation unit of the control section 400 causes the display device 240 to present the visual target at one point in the field of view and to gradually increase the brightness of the visual target. When the brightness of the visual target becomes equal to or higher than the predetermined brightness, the visual target becomes visible by the testee. At this time, the testee pushes the switch 420. Then, a signal indicating that the examinee has visually recognized the visual target, is transmitted from the switch 420 to the controller 400. Based on the signal transmitted from the switch 420, the sensitivity mapping unit of the controller 400 determines a value corresponding to the brightness of the visual target at the time of making the visual target visible, as the retina sensitivity at the point of the visual target presented. By performing a similar measurement for each point in the field of view, the sensitivity mapping unit of the controller 400 creates a map of the sensitivity of the retina 22 within the field of view.

The objective visual field test is performed as follows. First, the HM unit 100 of the vision testing device 10 is mounted on the testee's head. In this case, it is not necessary for the testee to hold the switch 420. The target presentation unit of the controller 400 causes the display device 240 to present the visual target at one point in the field of view and to gradually increase the brightness of the visual target. At the same time, the eyeball 20 of the testee is irradiated with the infrared light by the light source 310, and the imaging device 340 images the pupil 21 of the eyeball 20 of the testee. When the brightness of the visual target becomes equal to or higher than the predetermined brightness, the visual target becomes visible by the testee since the retina 22 of the testee senses the light of the visual target. At this time, the pupil of the testee is changed (miosis) according to the brightness of the target. The miosis detection unit of the controller 400 performs image analysis based on the image of the pupil 21 acquired by the imaging device 340, to thereby detect the miosis of the pupil 21 when the brightness of the visual target presented by the display device 240 becomes equal to or higher than the predetermined brightness. Then, when the miosis detection unit of the controller 400 detects the miosis of the pupil 21, the sensitivity mapping unit of the controller 400 sets the brightness of the visual target presented by the display device 240 at the time of detecting the miosis of the pupil 21 by the miosis detection unit, as the sensitivity of the retina 22. By performing a similar measurement for each point in the field of view, the sensitivity mapping unit of the controller 400 automatically creates a map of the sensitivity of the retina 22 within the field of view.

Further, in the objective visual field test, it is also acceptable to use a single threshold stimulation method, including: displaying a bright visual target at one point on the display surface of the display device 240, and creating a sensitivity map by observing a degree of reduction of a pupil diameter.

<Effect of Embodiments>

According to embodiments of the present invention, the following effect can be obtained.

(a) According to this embodiment, the optical axis 280a from the pupil 21 of the eyeball 20 to the mirror 220 in the display optical system 200, and the optical axis 280b from the mirror 220 to the display device 240 in the display optical system 200, are bent in a direction of mutually reflecting through the mirror 220. Thereby, the size of the vision testing device 10 as a whole can be decreased.

Here, for reference, problems of the display optical system in the head-mount type vision testing device will be described. In the head-mount type vision testing device, in order to present the visual target over a wide angle to the eyeball without increasing the size of the display device for presenting the visual target, it is necessary to increase the size of the display optical system that guides the light of the visual target to the retina of the eyeball, by combining a plurality of lenses or the like. When the display device is arranged so as to face the eyeball of the testee and the display optical system is linearly provided, only the display optical system protrudes in the forward direction of the testeet's head. As the display optical system becomes larger, the protrusion amount of the casing in the forward direction of the head also becomes larger. Therefore, there is a possibility that the size of the vision testing device as a whole becomes large in a distorted shape. Also, there is a possibility that the vision testing device becomes unstable when it is mounted on the testee's head. In contrast, according to this embodiment, the display optical system 200 is bent through the mirror 220. Thereby, even when the size of the display optical system 200 is increased, it is possible to prevent only the display optical system 200 from protruding in the forward direction of the testee's head, and the protrusion amount of the casing in the forward direction of the head can be suppressed. Accordingly, the size of the vision testing device 10 as a whole can be decreased. Further, the vision testing device 10 can be stable when it is mounted on the testee's head.

(b) According to this embodiment, the optical axis 280b from the mirror 220 to the display device 240 in the display optical system 200 is inclined toward the head side than a direction vertical to the optical axis 280a from the pupil 21 of the eyeball 20 to the mirror 220 in the display optical system 200. Thereby, it is possible to improve the weight balance of the vision testing device 10 as a whole.

For reference, explanation will be given here for a problem when the display device is arranged so as to face the eyeball of the testee and the display optical system is provided linearly, in the vision testing device in which the size of the display optical system is increased. In this case, as described above, only the display optical system protrudes in the forward direction of the testee's head. Therefore, the center of gravity of the display optical system is biased toward the front of the testee's head, and the weight balance of the vision testing device can not be maintained. In the head-mount type vision testing device, there is a possibility that the head of the testee will move. Therefore, if the weight balance of the vision testing device is poor, there is a possibility that the vision testing device will fall off or tilt from the testee's head. In contrast, according to this embodiment, the optical axis 280b at the bent side of the display optical system 200, is inclined toward the head side. Thus, even if the size of the display optical system 200 is increased, the center of gravity at the bent side of the display optical system 200 can be positioned close to the head side, and it is possible to prevent the center of gravity of the display optical system 200 from being biased toward the front of the testee's head. Accordingly, the weight balance of the vision testing device 10 can be improved as a whole. Even when the head of the testee moves, by positioning the center of gravity of the bent side of the display optical system 200 close to the head side, it is possible to suppress the vision testing device 10 from being falling off or tilted from the head.

(c) According to this embodiment, the first lens 210 has a large positive refractive power (power). Specifically, the focal length f1 of the first lens 210 satisfies the above formulas (2) and (3). Further, the power of the first lens 210 is 20D (diopter) or more and 60D or less. Thus, in the case of the backward light coming from the retina 22, all lights from the retina 22 over a wide angle can be converged by the first lens 210 within the range of the mirror 220.

Here, for reference, explanation will be given for a problem in the case where the power of the first lens is small.

When the power of the first lens is small, the ray from the retina may not be sufficiently converged at the position on the mirror side of the first lens, and may disperse at the position of the mirror, in the case of the backward ray from the retina. In this state, a part of the light from the retina is not reflected by the mirror and the image thereof is not formed at the position of the display device. In this case, in order to reflect all lights from the retina by the mirror, there is no choice but increase the size of the mirror, and there is a possibility that the size of the vision testing device is also increased. In contrast, in this embodiment, due to a large power of the first lens 210, the light flux of the principal ray from the retina 22 passing through the edge of the first lens 210 can be bent by the first lens 210 and can be focused (collected), for example at a position near the mirror 220, in the case of the backward ray from the retina 22. All lights from the retina 22 over a wide angle can be converged by the first lens 210 within the range of the mirror 220. Then, the light converged by the first lens 210 can be reflected by the mirror 220 and the image thereof can be formed at the position of the display device 240 by the second lens group 230. When the situation of these rays is reversely considered, that is, in the case of the forward ray from the display device 240, the visual target from the display device 240 having a predetermined size, can be presented to the eyeball 20 by the first lens 210 over the wide angle (angle of view). Further, since all lights from the retina 22 can be converged within the range of the mirror 220 by the first lens 210, it is possible to suppress the increase in the size of the mirror 220 itself and the size of the vision testing device 10 can be decreased.

<6. Modified Example, Etc.>

The present invention is not limited to the abovementioned content of the embodiments, and can be suitably modified in a range not departing from the gist of the invention.

In the abovementioned embodiment, explanation is given for a case where the controller 400 is provided on the rear head side of the mounting fixture 120, but the controller may be stored in the casing of the HM unit. Further, the controller may be provided separately from the HM unit.

In the abovementioned embodiment, explanation is given for a case where the first lens 210 of the display optical system 200 is composed of one lens, but the first lens may be a lens group composed of a plurality of lenses.

In the abovementioned embodiment, explanation is given for a case where the mirror 220 is a cold mirror, but the mirror may be a hot mirror or a dichroic mirror.

In the abovementioned embodiment, explanation is given for a case where the optical axis 280b from the mirror 220 to the display device 240 in the display optical system 200 is positioned vertically above the optical axis from the pupil 21 of the eyeball 20 to the mirror 220 in the display optical system 200, but the optical axis from the mirror to the display device in the display optical system may be positioned vertically below the optical axis from the pupil of the eyeball to the mirror in the display optical system.

In the abovementioned embodiment, explanation is given for a case where the display optical system 200 is composed of four lenses in total, and the observation optical system 300 is composed of two lenses in total (one of which is shared with the display optical system 200), but the number and the shape of the lenses constituting each optical system, the lens interval in an optical axis direction, and the like can be changed as necessary. However, in order to correct the chromatic aberration and an image magnification by combining the lens having a positive power and the lens having a negative power, the second lens group 230 is preferably composed of a plurality of lenses. Further, the mirror 220 may be a dichroic mirror.

Figure 5:
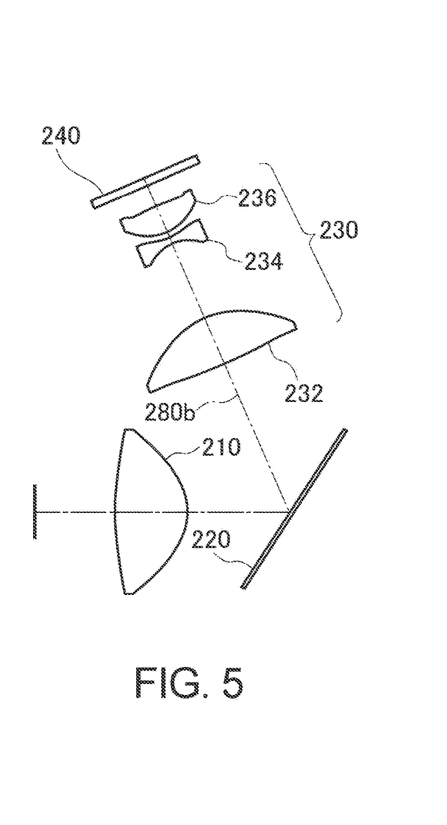
FIG. 5 is a schematic view showing another configuration example (modified example 1) of a display optical system.
Figure 6:
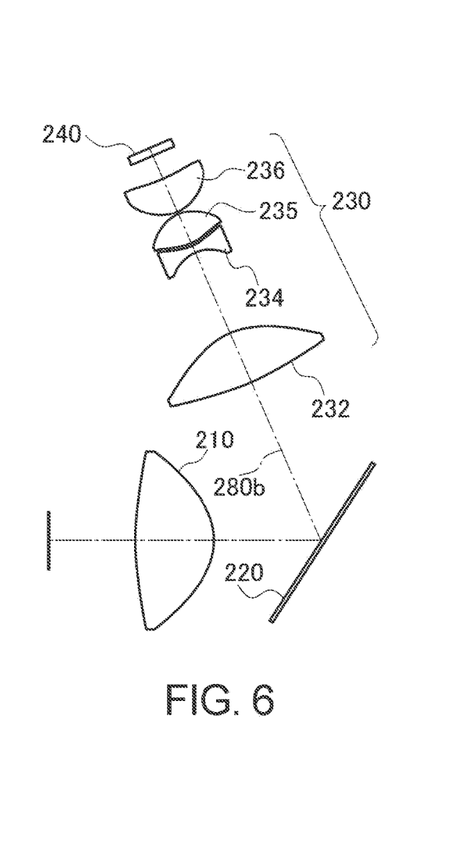
FIG. 6 is a schematic view showing another configuration example (modified example 2) of the display optical system.

Here, another configuration example of the display optical system will be described with reference to FIGS. 5 and 6. FIG. 5 is a schematic view showing another configuration example (modified example 1) of a display optical system. FIG. 6 is a schematic view showing another configuration example (modified example 2) of the display optical system.

As shown in FIG. 5, in the first modified example, the positive meniscus lens 236 belonging to the second lens group 230 of the display optical system 200 is set to be movable in the optical axis direction by a lens moving mechanism (not shown), which is different from the abovementioned embodiment. When this configuration is adopted, a diopter can be adjusted according to the visual acuity of the testee.

On the other hand, as shown in FIG. 6, the modified example 2 is different from the abovementioned embodiment, in a point that the second lens group 230 of the display optical system 200 is configured by using four lenses 232 to 236 in total by adding a positive lens 235, and in a point that the size of the display surface of the planar display device 240 is decreased. When this configuration is adopted, it becomes possible to display the visual target more clearly for the testee. Further, in this configuration, by making the positive meniscus lens 236 movable in the optical axis direction, the diopter can be adjusted in accordance with the visual acuity of the testee.

EXAMPLES

Figure 3A:
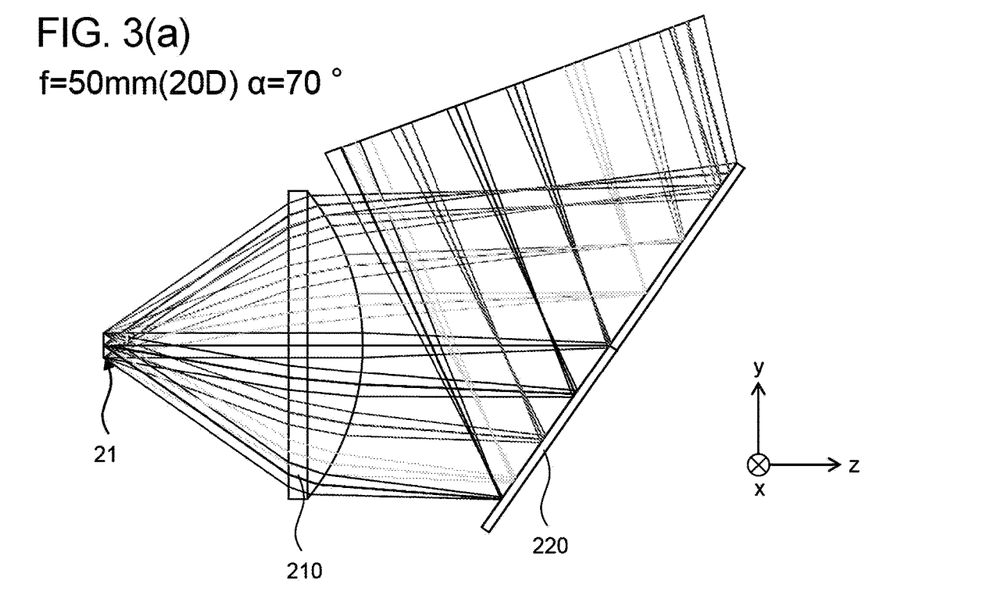
FIG. 3(a) is a ray diagram of example 1, and (b) is a ray diagram of example 2.
Figure 3B:
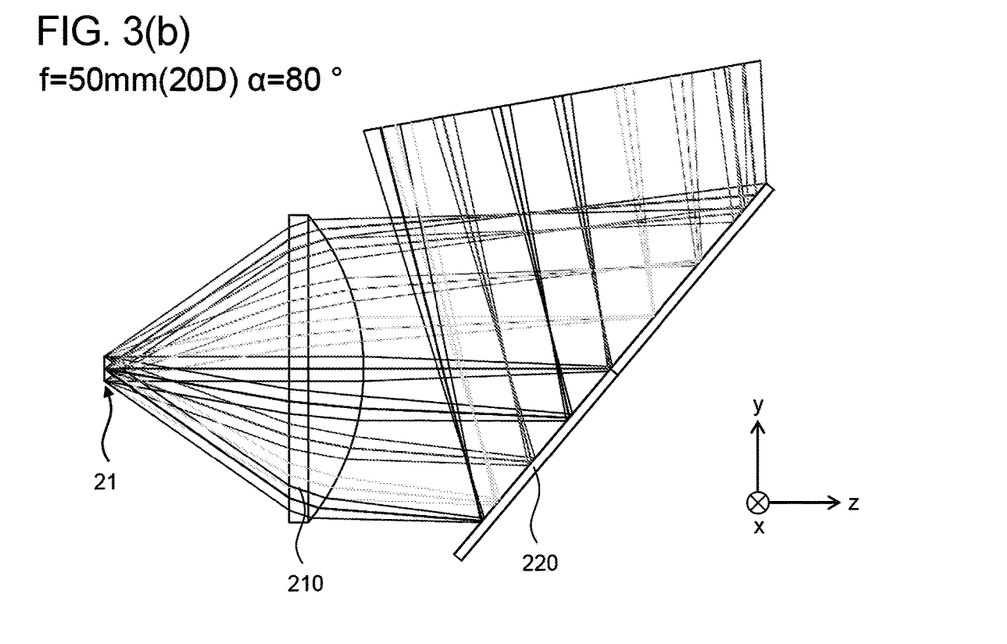
Figure 4A:
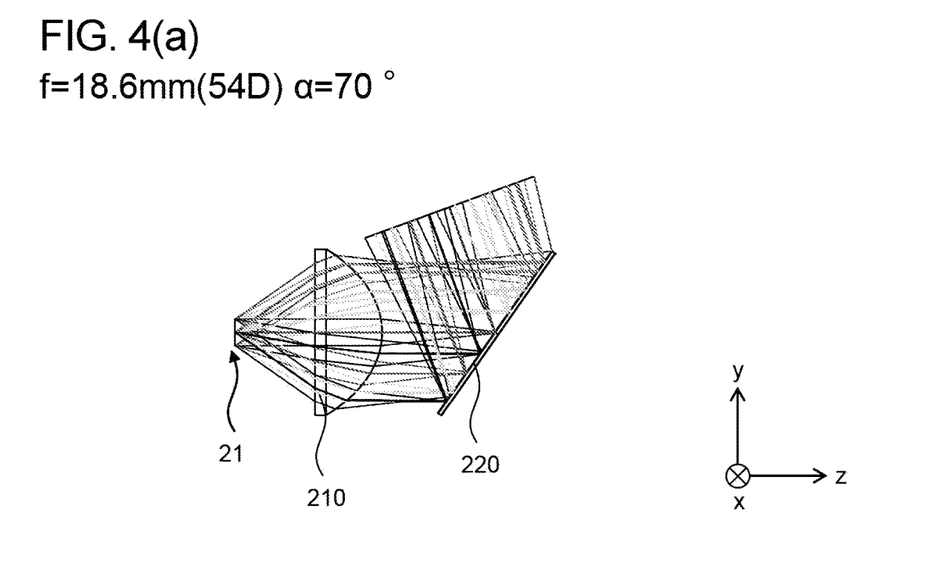
FIG. 4(a) is a ray diagram of example 3, and (b) is a ray diagram of example 4.
Figure 4B:
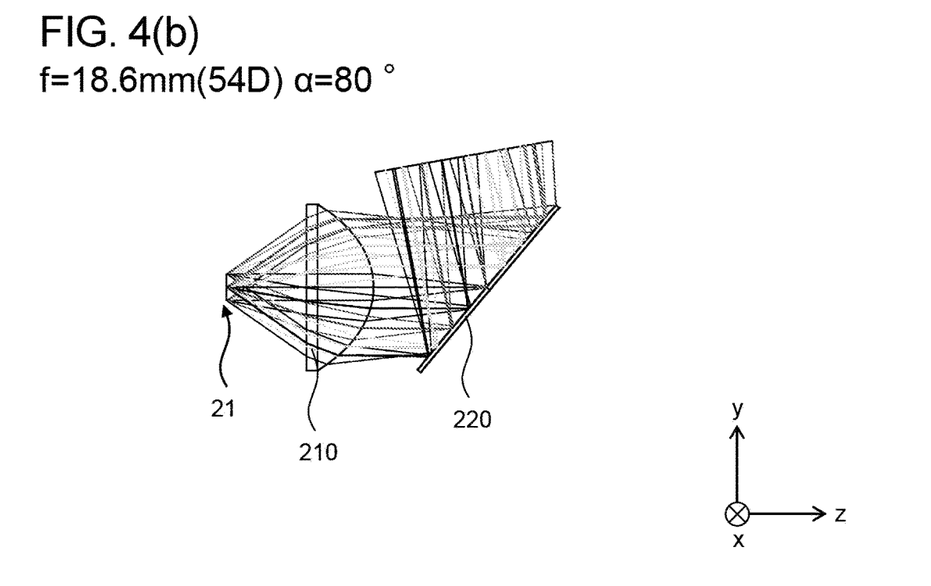

Next, examples according to the present invention will be described with reference to FIGS. 3 and 4. FIG. 3($a$) is a ray diagram of example 1, and (b) is a ray diagram of example 2. FIG. 4($a$) is a ray diagram of example 3, and (b) is a ray diagram of example 4. FIGS. 3($a$) to 4($b$) show the results of a simulation by reverse ray tracing with the pupil 21 as an exit pupil. In FIGS. 3($a$) to 4($b$), the second lens group 230 is omitted. Further, in FIGS. 3($a$) to 4($b$), the ratio of the size and interval of the first lens and the mirror was set to be equal to an actual ratio. A vertical direction was defined as a y-direction, a direction vertical to the y-direction and vertical to the optical axis of the first lens 210 was defined as an x-direction, and a direction vertical to the y-direction and parallel to the optical axis of the first lens 210 was defined as a z-direction.

Here, in order to study an influence of the power of the first lens 210, simulations of examples 1 to 4 were performed under the following conditions.

Example 1

First lens focal length $f$=50 mm(power=20$D$)

$\alpha$=70°

Example 2

First lens focal length $f$=50 mm(power=20$D$)

$\alpha$=80°

Example 3

First lens focal length $f$=18.6 mm(power=54$D$)

$\alpha$=70°

Example 4

First lens focal length $f$=18.6 mm(power=54$D$)

$\alpha$=80°

In each of the examples, a full angle of view of the ray traveling from the pupil 21 toward the first lens 210 was set to 70°.

Examples 1 and 2

In example 1 of FIG. 3(a) and example 2 of FIG. 3(b), it was confirmed that the light flux of the principal ray emitted from the pupil 21 was collected near the mirror 220 and the light fluxes of all principal rays extending over the full angle of view of 70° were converged within the range of the mirror 220.

Further, in example 1 of FIG. 3(a) and example 2 of FIG. 3(b), a required diameter of the mirror 220 in the x-direction was about 54 mm. Since the required diameter of the mirror 220 in the x-direction was close to the inter-pupil distance (about 50 mm), the required diameter of the mirror 220 in the x-direction was a limit size such that members such as the lens barrel that holds the mirror 220 for each of both eyes do not interfere with each other. Accordingly, it was confirmed that a lower limit of the power of the first lens 210 was 20D.

Further, in example 2 where $\alpha$=80° in FIG. 3(b), the required diameter of the mirror 220 in the y-direction was 79 mm. In contrast, In example 1 where $\alpha$=70° in FIG. 3(a), the required diameter of the mirror 220 in the y-direction was 72 mm. Accordingly, it was confirmed that by satisfying $\alpha \leq 70°$, the range of the light irradiated from the first lens 210 to the mirror 220 could be decreased, and the required diameter of the mirror 220 in the vertical direction could be decreased. In example 1 where $\alpha$=70° in FIG. 3(a), it was confirmed that the light emitted from the pupil 21 was reflected by the mirror 220 closer to the head side than the example 2 where $\alpha$=80° in FIG. 3(b). Accordingly, it was confirmed that by satisfying $\alpha \leq 70°$, the center of gravity of the second lens group 230 and the display device 240 could be arranged so as to be further close to the head side.

Examples 3 and 4

Also in example 3 of FIG. 4(a) and example 4 of FIG. 4(b), it was confirmed that the light flux of the principal ray emitted from the pupil 21 was collected near the mirror 220, and the light flux of all principal rays extending over the full angle of view of 70° was converged within the range of the mirror 220.

Further, it was confirmed that by increasing the power of the first lens 210, the size of each of the optical systems of example 3 of FIG. 4(a) and example 4 of FIG. 4(b) could be more decreased than the size of each of the optical systems of example 1 shown in FIG. 3(a) and example 2 shown in FIG. 3(b).

On the other hand, in example 3 of FIG. 4(a) and example 4 of FIG. 4(b), since the power of the first lens 210 was increased, the distance between the pupil 21 and the first lens 210 was decreased, and therefore the distance between the pupil 21 and the first lens 210 was a limit distance at which the first lens 210 did not interfere with eyelashes and eyelids of the testee. Accordingly, it was confirmed that an upper limit value of the power of the first lens 210 was 60D.

DESCRIPTION OF SIGNS AND NUMERALS

10 Vision testing device
20 Eyeball
21 Pupil
22 Retina
100 Head mount (HM) unit
110 Casing (mounting body)
120 Mounting fixture
200 Display optical system
210 First lens
220 Mirror
230 Second lens group
232 Positive lens
234 Negative lens
235 Positive lens
236 Positive meniscus lens
240, 240R, 230L Display device
280a, 280b Optical axis
300 Observation optical system
310 Light source
320 Imaging lens
340 Imaging device
380a Optical axis
400 Controller (computer unit)
420 Switch

The invention claimed is:

1. A vision testing device, which is a head-mount type vision testing device mounted on a testee's head, comprising:
   a display device that presents a visual target to an eyeball of the testee;
   a display optical system that guides a light of the visual target presented on the display device, to a retina of the eyeball;
   an imaging device configured to transmit an image of the eyeball; and
   an observation optical system that guides light from the eyeball to the imaging device such that the imaging device is enabled to image the eyeball, wherein:
   the display optical system includes a mirror that reflects a light of a specific wavelength and transmits the other light,
   an optical axis from a pupil of the eyeball to the mirror in the display optical system and an optical axis from the pupil to the mirror in the observation optical system, coincide with each other,
   the optical axis from the pupil of the eyeball to the mirror in the display optical system and an optical axis from the mirror to the display device in the display optical system, are at an inclined angle with respect to each other,
   the display optical system further comprises:
   a first lens provided between the eyeball and the mirror and having an optical axis passing through a center of the pupil of the eyeball; and
   a second lens group provided between the mirror and the display device and provided on an optical axis in a direction reflecting through the mirror with respect to the optical axis of the first lens, the observation optical system shares the first lens with the display optical system, and a focal length of the first lens is shorter than an optical distance from the first lens to the second lens group.

2. The vision testing device according to claim 1, wherein the optical axis from the mirror to the display device in the display optical system, is inclined to toward a head side than a direction vertical to the optical axis from a pupil of the eyeball to the mirror in the display optical system.

3. The vision testing device according to claim 1, wherein when an angle formed by the optical axis from the pupil of the eyeball to the mirror in the display optical system, and the optical axis from the mirror to the display device in the display optical system, is represented by a, the following formula (1) is satisfied:

$$40° < \alpha < 90° \tag{1}$$

4. The vision testing device according to claim 1, wherein a power of the first lens is 20D or more and 60D or less.

5. The vision testing device according to claim 1, wherein a diagonal length of the display device is 1.5 inches or less.

* * * * *